US012370353B2

United States Patent
Congdon et al.

(10) Patent No.: US 12,370,353 B2
(45) Date of Patent: Jul. 29, 2025

(54) AGENT DELIVERY DEVICE

(71) Applicant: Boston Scientific Scimed, Inc., Maple Grove, MN (US)

(72) Inventors: Daniel Congdon, Hudson, MA (US); Matthew Robert Jagelski, Marlborough, MA (US); Laurie A. Lehtinen, Boylston, MA (US); Andrew Pic, Northboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1141 days.

(21) Appl. No.: 17/123,708

(22) Filed: Dec. 16, 2020

(65) Prior Publication Data

US 2021/0187190 A1    Jun. 24, 2021

Related U.S. Application Data

(60) Provisional application No. 62/951,426, filed on Dec. 20, 2019.

(51) Int. Cl.
*A61M 37/00* (2006.01)
*A61M 5/155* (2006.01)
(Continued)

(52) U.S. Cl.
CPC ........ *A61M 37/0069* (2013.01); *A61M 5/155* (2013.01); *A61M 5/31586* (2013.01); *A61M 39/22* (2013.01); *A61M 2205/8206* (2013.01)

(58) Field of Classification Search
CPC .............. A61M 37/0069; A61M 5/155; A61M 5/31586; A61M 2205/8206; A61M 39/22
See application file for complete search history.

(56) References Cited

U.S. PATENT DOCUMENTS

| 471,854 A | | 3/1892 | Howard | |
| 780,147 A | * | 1/1905 | Wilcox et al. | .... A61M 5/31586 604/224 |

(Continued)

FOREIGN PATENT DOCUMENTS

| CN | 1416357 A | 5/2003 |
| CN | 101401956 B | 11/2012 |

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

(Continued)

*Primary Examiner* — Nathan R Price
*Assistant Examiner* — Mark A Igel
(74) *Attorney, Agent, or Firm* — Bookoff McAndrews, PLLC

(57) ABSTRACT

A medical device comprising a housing defining at least one enclosure for storing agent in a first form, a force applicator within the housing and adjacent the enclosure, a drive mechanism for moving the agent toward the force applicator, wherein the force applicator defines a surface for applying a force to the agent to separate the agent into particles smaller than a size of the first form, and wherein the device defines a lumen for receiving the particles from the force applicator and for receiving a pressurized fluid to propel the particles through the lumen.

19 Claims, 5 Drawing Sheets

(51) Int. Cl.
*A61M 5/315* (2006.01)
*A61M 39/22* (2006.01)

(56) References Cited

U.S. PATENT DOCUMENTS

| | | | |
|---|---|---|---|
| 881,238 A | 3/1908 | Hasbrouck | |
| 1,145,520 A | 7/1915 | Smith | |
| 1,599,959 A | 9/1926 | Buheiji | |
| 1,718,596 A * | 6/1929 | Smith | A61M 5/24 |
| | | | 222/391 |
| 1,732,566 A | 10/1929 | McKendrick | |
| 2,151,418 A | 3/1939 | Bolté | |
| 2,185,927 A | 6/1940 | Shelanski | |
| 2,478,715 A | 8/1949 | Schmitt | |
| 2,623,519 A | 12/1952 | Cohen | |
| 2,632,444 A * | 3/1953 | Kas | A61M 37/0069 |
| | | | 604/63 |
| 2,883,984 A * | 4/1959 | Candido, Jr. | A61M 37/0069 |
| | | | 604/61 |
| 3,669,113 A | 6/1972 | Altounyan et al. | |
| 3,940,061 A | 2/1976 | Gimple et al. | |
| 4,077,406 A * | 3/1978 | Sandhage | A61M 37/0069 |
| | | | 604/61 |
| 4,184,258 A | 6/1980 | Barrington et al. | |
| 4,400,170 A | 8/1983 | McNaughton et al. | |
| 4,427,450 A | 1/1984 | Kostansek | |
| 4,457,329 A | 7/1984 | Werley et al. | |
| 4,762,515 A * | 8/1988 | Grimm | A61M 37/0069 |
| | | | 74/411 |
| 4,806,167 A | 2/1989 | Raythatha | |
| 5,215,221 A | 6/1993 | Dirksing | |
| 5,231,983 A | 8/1993 | Matson et al. | |
| 5,273,531 A | 12/1993 | Knoepfler | |
| 5,312,331 A | 5/1994 | Kneopfler | |
| 5,312,333 A | 5/1994 | Churinetz et al. | |
| 5,366,122 A | 11/1994 | Guentert et al. | |
| 5,445,612 A * | 8/1995 | Terakura | A61M 13/00 |
| | | | 604/24 |
| 5,469,843 A * | 11/1995 | Hodson | A61M 15/0021 |
| | | | 128/203.15 |
| 5,470,311 A | 11/1995 | Setterstrom et al. | |
| 5,694,920 A * | 12/1997 | Abrams | A61M 11/001 |
| | | | 128/200.16 |
| 5,884,621 A | 3/1999 | Matsugi et al. | |
| 5,951,531 A | 9/1999 | Ferdman et al. | |
| 6,003,512 A | 12/1999 | Gerde | |
| 6,415,790 B1 * | 7/2002 | Leedom | A61M 15/0048 |
| | | | 128/203.15 |
| 6,484,750 B1 | 11/2002 | Foos et al. | |
| 6,554,022 B2 | 4/2003 | Wakeman | |
| 6,589,087 B2 | 7/2003 | Mackal et al. | |
| 6,684,917 B2 | 2/2004 | Zhu et al. | |
| 6,708,712 B2 | 3/2004 | Wakeman | |
| 6,716,190 B1 | 4/2004 | Glines et al. | |
| 6,799,571 B1 | 10/2004 | Hughes et al. | |
| 6,871,647 B2 * | 3/2005 | Allan | A61M 15/0071 |
| | | | 128/203.15 |
| 7,178,547 B2 | 2/2007 | Mackal | |
| 7,311,270 B2 | 12/2007 | Kapila | |
| 7,334,598 B1 | 2/2008 | Hollars | |
| 7,361,300 B2 | 4/2008 | Kelly et al. | |
| 7,427,607 B2 | 9/2008 | Suzuki | |
| 7,455,248 B2 | 11/2008 | Kablik et al. | |
| 7,461,649 B2 | 12/2008 | Gamard et al. | |
| 7,544,177 B2 | 6/2009 | Gertner | |
| 7,563,299 B2 | 7/2009 | Baptista da Costa et al. | |
| 7,673,647 B2 | 3/2010 | Mackal | |
| 7,841,338 B2 | 11/2010 | Dunne et al. | |
| 7,892,205 B2 | 2/2011 | Palasis et al. | |
| 7,921,874 B2 | 4/2011 | Tekulve et al. | |
| 8,037,880 B2 | 10/2011 | Zhu et al. | |
| 8,097,071 B2 | 1/2012 | Burgess et al. | |
| 8,118,777 B2 | 2/2012 | Ducharme et al. | |
| 8,269,058 B2 | 9/2012 | McCarthy et al. | |
| 8,313,474 B2 | 11/2012 | Campbell et al. | |
| 8,360,276 B2 | 1/2013 | Rogier et al. | |
| 8,361,054 B2 | 1/2013 | Ducharme et al. | |
| 8,496,189 B2 | 7/2013 | Lomond et al. | |
| 8,673,065 B2 | 3/2014 | Burgess et al. | |
| 8,721,582 B2 | 5/2014 | Ji | |
| 8,728,032 B2 | 5/2014 | Ducharme et al. | |
| 8,741,335 B2 | 6/2014 | McCarthy | |
| 8,827,980 B2 | 9/2014 | Ji | |
| 8,910,627 B2 | 12/2014 | Iwatschenko et al. | |
| 8,951,565 B2 | 2/2015 | McCarthy | |
| 9,028,437 B2 | 5/2015 | Ott et al. | |
| 9,089,658 B2 | 7/2015 | Dunne et al. | |
| 9,101,744 B2 | 8/2015 | Ducharme | |
| 9,107,668 B2 | 8/2015 | Melsheimer et al. | |
| 9,132,206 B2 | 9/2015 | McCarthy | |
| 9,204,957 B2 | 12/2015 | Gregory et al. | |
| 9,205,170 B2 | 12/2015 | Lucchesi et al. | |
| 9,205,207 B2 | 12/2015 | Ji | |
| 9,205,240 B2 | 12/2015 | Greenhalgh et al. | |
| 9,308,584 B2 | 4/2016 | Burgess et al. | |
| 9,310,812 B2 | 4/2016 | Costle et al. | |
| 9,375,533 B2 | 6/2016 | Ducharme et al. | |
| 9,492,646 B2 | 11/2016 | Hoogenakker et al. | |
| 9,517,976 B2 | 12/2016 | Mackal | |
| 9,545,490 B2 | 1/2017 | Iwatschenko et al. | |
| 9,555,185 B2 | 1/2017 | Foster et al. | |
| 9,629,966 B2 | 4/2017 | Ji | |
| 9,636,470 B2 * | 5/2017 | Pohlmann | A61M 16/202 |
| 9,707,359 B2 | 7/2017 | Kubo | |
| 9,713,682 B2 | 7/2017 | Eistetter et al. | |
| 9,717,897 B2 | 8/2017 | Rogier | |
| 9,821,084 B2 | 11/2017 | Diegelmann et al. | |
| 9,839,772 B2 | 12/2017 | Ducharme | |
| 9,839,774 B2 | 12/2017 | Bonaldo | |
| 9,846,439 B2 | 12/2017 | Carman et al. | |
| 9,867,931 B2 | 1/2018 | Gittard | |
| 9,976,660 B2 | 5/2018 | Stanton et al. | |
| 10,004,690 B2 | 6/2018 | Lee et al. | |
| 10,010,705 B2 | 7/2018 | Greenhalgh et al. | |
| 10,017,231 B2 | 7/2018 | Fawcett, Jr. | |
| 10,036,617 B2 | 7/2018 | Mackal | |
| 10,065,004 B2 * | 9/2018 | Eder | A61C 3/025 |
| 10,173,019 B2 | 1/2019 | Kaufmann et al. | |
| 10,384,049 B2 | 8/2019 | Stanton et al. | |
| 10,463,811 B2 | 11/2019 | Lee et al. | |
| 10,507,293 B2 | 12/2019 | Goodman et al. | |
| 10,646,706 B2 | 5/2020 | Rogier | |
| 10,730,595 B2 | 8/2020 | Fawcett | |
| 10,751,523 B2 | 8/2020 | Rogier | |
| 10,806,853 B2 | 10/2020 | Gittard | |
| 10,850,814 B2 | 12/2020 | Fawcett | |
| 10,994,818 B2 * | 5/2021 | Hernandez | B63C 9/24 |
| 2002/0053344 A1 * | 5/2002 | Davies | A61M 15/0045 |
| | | | 128/203.15 |
| 2004/0107963 A1 | 6/2004 | Finlay et al. | |
| 2004/0249359 A1 | 12/2004 | Palasis et al. | |
| 2005/0044755 A1 * | 3/2005 | Rayner | E02F 9/2858 |
| | | | 37/452 |
| 2005/0121025 A1 | 6/2005 | Gamard et al. | |
| 2005/0147656 A1 | 7/2005 | McCarthy et al. | |
| 2005/0220721 A1 | 10/2005 | Kablik et al. | |
| 2006/0004314 A1 | 1/2006 | McCarthy et al. | |
| 2006/0038027 A1 * | 2/2006 | O'Connor | B05B 7/066 |
| | | | 239/589 |
| 2006/0213514 A1 | 9/2006 | Price et al. | |
| 2006/0247578 A1 | 11/2006 | Arguedas et al. | |
| 2007/0056586 A1 | 3/2007 | Price et al. | |
| 2007/0066920 A1 | 3/2007 | Hopman et al. | |
| 2007/0066924 A1 | 3/2007 | Hopman et al. | |
| 2007/0082023 A1 | 4/2007 | Hopman et al. | |
| 2007/0125375 A1 | 6/2007 | Finlay et al. | |
| 2007/0151560 A1 | 7/2007 | Price et al. | |
| 2007/0083137 A1 | 8/2007 | Hopman et al. | |
| 2007/0199824 A1 | 8/2007 | Hoerr et al. | |
| 2008/0021374 A1 | 1/2008 | Kawata | |
| 2008/0103564 A1 | 5/2008 | Burkinshaw et al. | |
| 2008/0192565 A1 * | 8/2008 | Johnson | B01F 31/265 |
| | | | 366/109 |

(56) References Cited

U.S. PATENT DOCUMENTS

| | | | |
|---|---|---|---|
| 2008/0287907 A1 | 11/2008 | Gregory et al. | |
| 2009/0018505 A1* | 1/2009 | Arguedas | G01F 11/022 |
| | | | 604/131 |
| 2009/0101144 A1 | 4/2009 | Gamard et al. | |
| 2009/0155342 A1 | 6/2009 | Diegemann et al. | |
| 2009/0281486 A1 | 11/2009 | Ducharme | |
| 2010/0121261 A1 | 5/2010 | Kablik et al. | |
| 2010/0305505 A1 | 12/2010 | Ducharme et al. | |
| 2011/0073200 A1 | 3/2011 | Overvaag et al. | |
| 2011/0270156 A1 | 11/2011 | Hassan et al. | |
| 2011/0274726 A1 | 11/2011 | Guo et al. | |
| 2011/0308516 A1 | 12/2011 | Price et al. | |
| 2012/0296259 A1 | 11/2012 | Imran | |
| 2013/0218072 A1* | 8/2013 | Kubo | A61M 13/00 |
| | | | 604/58 |
| 2014/0271491 A1 | 9/2014 | Gittard et al. | |
| 2015/0094649 A1 | 4/2015 | Gittard | |
| 2015/0125513 A1 | 5/2015 | McCarthy | |
| 2016/0375202 A1 | 12/2016 | Goodman et al. | |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1* | 7/2018 | Smith | A61M 13/00 |
| 2018/0214160 A1 | 8/2018 | Hoskins et al. | |
| 2018/0339144 A1* | 11/2018 | Greenhalgh | A61M 35/003 |
| 2019/0134366 A1 | 5/2019 | Erez et al. | |
| 2019/0217315 A1 | 7/2019 | Maguire et al. | |
| 2019/0232030 A1* | 8/2019 | Pic | A61B 17/00491 |
| 2021/0024187 A1 | 1/2021 | Fawcett et al. | |
| 2021/0069485 A1 | 3/2021 | Rogier | |
| 2021/0162122 A1* | 6/2021 | Pic | A61M 5/16804 |
| 2021/0353912 A1* | 11/2021 | Kiev | A61M 25/0631 |

FOREIGN PATENT DOCUMENTS

| | | | |
|---|---|---|---|
| CN | 107929892 A | 4/2018 | |
| DE | 60215438 T2 | 8/2007 | |
| EP | 0469814 A1 | 2/1992 | |
| EP | 1033543 B1 * | 11/2007 | B64G 1/402 |
| EP | 3052168 B1 | 11/2019 | |
| GB | 1404338 A | 8/1975 | |
| JP | H07118305 A | 5/1995 | |
| WO | WO-9947199 A1 * | 9/1999 | A61M 11/001 |
| WO | 03013552 A1 | 2/2003 | |
| WO | 2004066806 A2 | 8/2004 | |
| WO | 2005062896 A2 | 7/2005 | |
| WO | 2006071649 A2 | 7/2006 | |
| WO | 2006088912 A2 | 8/2006 | |
| WO | 2008033462 A2 | 3/2008 | |
| WO | 2009061409 A1 | 5/2009 | |
| WO | 2015050814 A1 | 4/2015 | |
| WO | 2018157772 A1 | 9/2018 | |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, Cook, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

RETSCH GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

International Search Report and Written Opinion issued in related PCT/US2020/065271, dated Mar. 29, 2021 (English, 13 pages).

* cited by examiner

AGENT DELIVERY DEVICE

CROSS-REFERENCE TO RELATED APPLICATIONS

This application claims the benefit of priority from U.S. Provisional Application No. 62/951,426, filed on Dec. 20, 2019, which is incorporated by reference herein in its entirety.

TECHNICAL FIELD

The present disclosure relates generally to a medical device that administers an agent. More particularly, at least some embodiments of the present disclosure relate to a medical device configured to be loaded with a therapeutic agent, separate the loaded agent into a smaller form, and then deliver that agent via a lumen of the medical device.

BACKGROUND

In certain medical procedures, it may be necessary to stop bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered by a device inserted into the working channel of the endoscope. Agent delivery may be achieved through mechanical systems, for example. Such systems, however, may require numerous steps or actuations to achieve delivery, may not achieve a desired rate of agent delivery or a desired dosage of agent, may result in the agent clogging portions of the delivery device, may result in inconsistent dosing of agent, or may not result in the agent reaching the treatment site deep within the GI tract. The current disclosure may solve one or more of these issues or other issues in the art.

SUMMARY OF THE DISCLOSURE

According to an example, a medical device may include a housing defining at least one enclosure for storing agent in a first form, a force applicator within the housing and adjacent the enclosure, a drive mechanism for moving the agent toward the force applicator. The force applicator may define a surface for applying a force to the agent to separate the agent into particles smaller than a size of the first form. The device may define a lumen for receiving the particles from the force applicator and for receiving a pressurized fluid to propel the particles through the lumen. The force applicator may include a round gear including a plurality of teeth about a circumference of the gear. The drive mechanism may include two rotatable wheels to receive the agent between the two rotatable wheels, and may be connected to a trigger outside the housing. The actuation of the trigger may cause rotation of the two rotatable wheels.

In another example, the medical device may further include a fluid source, e.g., gas, for providing the pressurized fluid, wherein the fluid source may be connected to the lumen via a fluid channel, and wherein the fluid channel may be connected to a portion of the lumen distal to the force applicator. The fluid channel may include a valve configured to open or close a flow of pressurized fluid from the fluid source to the lumen. The valve may coupled to the trigger configured to at least open/close the valve.

In another example, the medical device may further include a first gear coupled to a surface of the force applicator, wherein the first gear is configured to rotate simultaneously with the force applicator, in a same direction, and a lever coupled to the housing, wherein an end of the lever includes a second gear, and the second gear and the first gear are connected in series via a linking gear positioned in between the first gear and the second gear, wherein actuation of the lever rotates the second gear, which rotates the linking gear, which rotates the first gear and the force applicator. Actuation of the lever may also actuate a trigger to supply a pressurized fluid to the lumen. Each throw, e.g., pivoted rotation, of the lever may rotate the force applicator by a consistent degree to supply a substantially consistent amount of particles to the lumen.

In another example, the medical device may further include an electric motor coupled to the force applicator, wherein the electric motor is configured to rotate the force applicator, and a battery electrically connected to the electric motor and a trigger, wherein the trigger is configured to act as an electrical switch that powers the electric motor via the battery. Actuation of the trigger may continuously rotate the force applicator and continuously supply pressurized fluid to the lumen from the fluid source, until the trigger is released.

In another example, the housing of the medical device may include a holster defining a plurality of enclosures for storing the agent, wherein the holster is rotatable relative to other portions of the housing and the lumen. The housing may include a chamber below the holster, and a channel between the chamber and the lumen so that there is fluid communication between the chamber and the lumen. The drive mechanism may include a rotation of the holster so that one of the plurality of enclosures aligns with the chamber, thereby delivering the agent from one of the enclosures to the chamber. The force applicator may include a wedge that obtrudes into the chamber, and the wedge may be configured to separate the agent in the chamber into particles.

According to another example, a medical device may include a housing defining at least one enclosure for storing agent in a first form, a force applicator within the housing and adjacent the enclosure, a drive mechanism for moving the agent toward the force applicator, wherein the force applicator includes a plurality of teeth for applying a force to the agent to separate the agent into particles smaller than a size of the first form, wherein the force applicator includes a first gear, and a lever coupled to the housing. The lever may include a second gear, and the second gear and the first gear may be coupled so that pulling the lever causes the second gear to rotate the first gear and the force applicator, separating the agent into the particles. The device may define a lumen for receiving the particles from the force applicator and for receiving a pressurized fluid to propel the particles through the lumen. The drive mechanism may be connected to a trigger outside the housing, and actuation of the trigger may operate the drive mechanism.

In another example, the medical device may further include a fluid source for providing the pressurized fluid, wherein the fluid source is connected to the lumen via a fluid channel, wherein the fluid channel includes a valve configured to open or close a flow of pressurized fluid from the fluid source to the lumen, wherein the valve is coupled to a trigger configured to at least open/close the valve, and wherein the trigger is located outside of the housing. Actuation of the lever may actuate a trigger to supply the pressurized fluid to the lumen.

According to an example, a method of administering agent via a medical device may include positioning a lumen of the medical device so that a distal end of the lumen is adjacent to a targeted site, wherein the device further includes a housing defining at least one enclosure storing the agent in a first form, a force applicator within the housing and adjacent the enclosure, and a drive mechanism for moving the agent toward the force applicator, providing a pressurized fluid to the lumen, and delivering the agent towards the force applicator via the drive mechanism, thereby separating the agent into particles smaller than a size of the first form via the force applicator, and feeding the lumen with the particles.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

The present disclosure may solve one or more of the limitations in the art. The scope of the disclosure, however, is defined by the attached claims and not the ability to solve a specific problem. The present disclosure is drawn to medical devices configured to be loaded with agent(s), e.g., therapeutic agents, that crush or separate the loaded agent(s) into smaller particles, and administer said particles to a targeted site, among other aspects. The agent may be in any first form, e.g., a rod, a pellet, prior to it being separated or crushed into a smaller form, such as a powder of loose particles, and delivered to a lumen receiving a stream of propellant/pressurized fluid, e.g., $CO_2$, nitrogen, air, etc. Said medical devices may help increase the consistency of particle size and particle delivery of agent, e.g., hemostatic powder, and may also help reduce variation that is inherent in conventional fluid-driven powder/particle mixing and delivery systems.

Figure 1A:
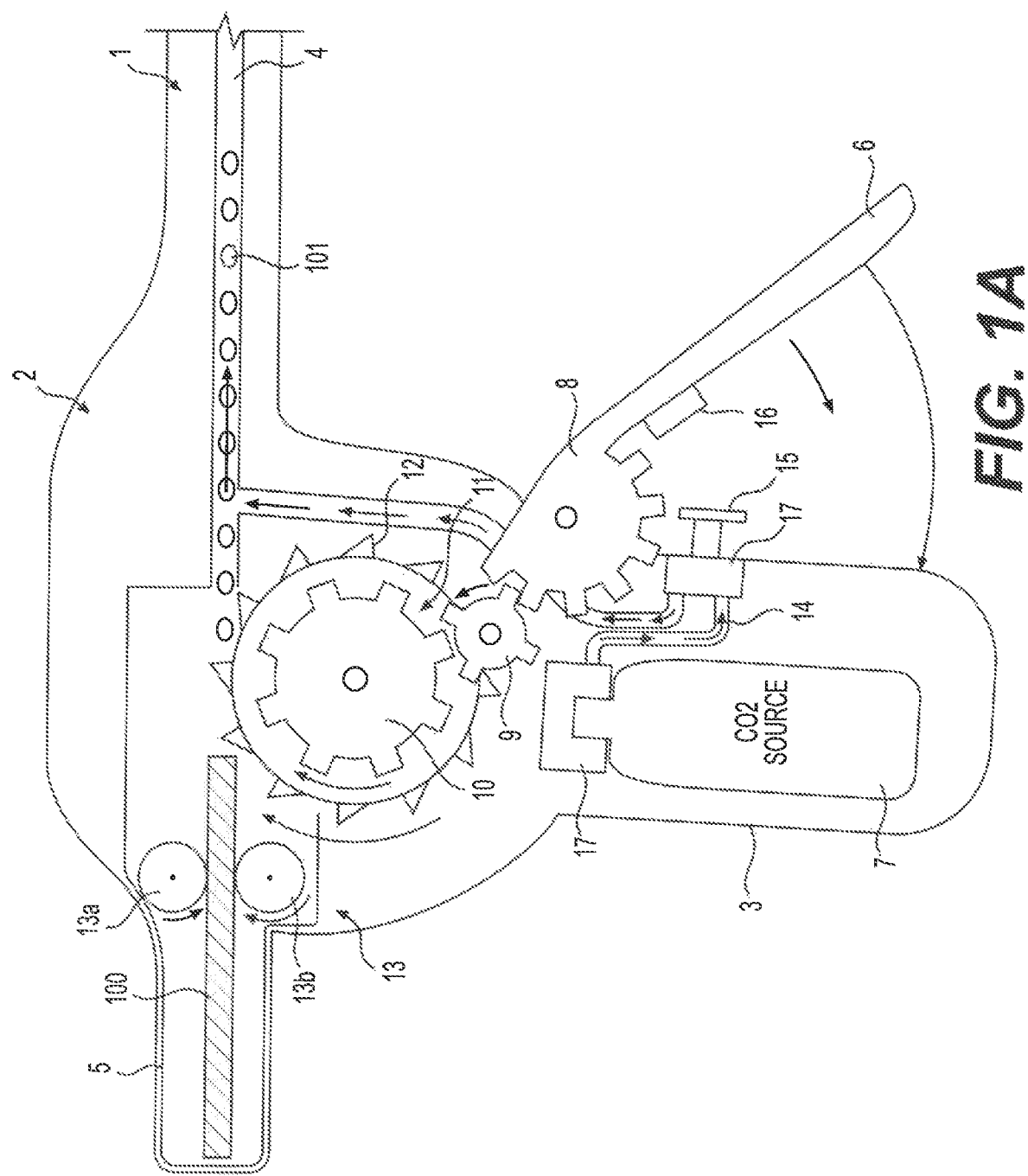
FIGS. 1A-1B are cross-sectional views of a medical device, according to different embodiments.
Figure 1B:
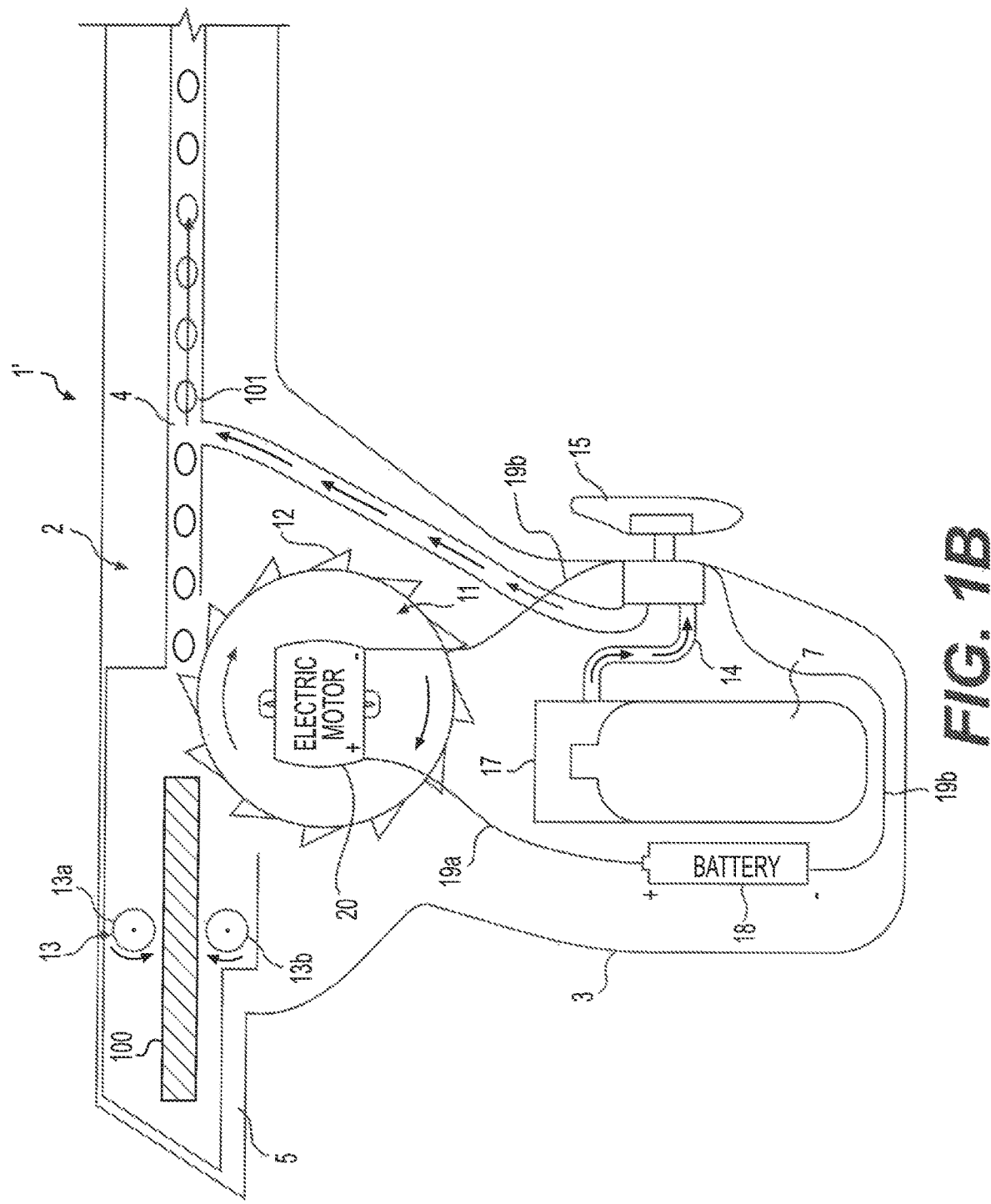
Figure 2:
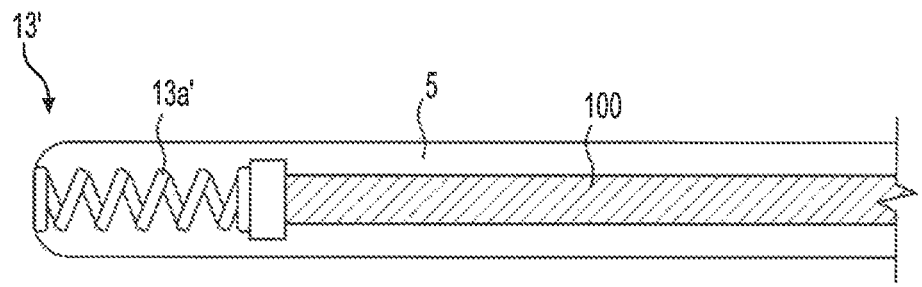
FIG. 2 is a cross-sectional view of an enclosure and a feeding mechanism of a medical device, according to an embodiment.

FIG. 1A illustrates an exemplary embodiment of medical device 1 in further detail. Medical device 1 includes a housing 2 defining at least one enclosure 5 for storing agent 100 in a first form, e.g., a rod or other single-piece shaped form of an agent, a force applicator 11 within housing 2 and adjacent enclosure 5, and a drive mechanism 13 configured for moving or propelling agent 100 towards force applicator 11. Enclosure 5 may be pre-loaded with agent 100, or enclosure 5 may include an opening/mechanism by which it may be loaded with agent 100. Force applicator 11 defines a surface, e.g., a surface of each of a plurality of teeth 12 along its circumference, for applying a force to agent 100 to separate it into particles 101 smaller than its first form. Instead of teeth 12 about its circumference, force applicator 11 could include serrations, barbs, or any other sharp or roughened surface capable of separating agent into powder/particle form. Drive mechanism 13 includes two wheels 13a and 13b positioned directly below and above one another, with sufficient space between one another to receive agent 100. Drive mechanism 13 may be within enclosure 5, in which agent 100 is stored. Drive mechanism 13 moves agent 100 towards force applicator 11 as wheel 13a rotates counter-clockwise and wheel 13b rotates clockwise. However, drive mechanism 13 is not limited to wheels 13a and 13b, and may be any suitable mechanism for advancing agent 100. Similarly, force applicator 11 may be any suitable mechanism for separating/crushing agent 100 into particles 101, such as, round grinders, worm gears, or augers. In some other embodiments, device 1 may include a plurality of force applicators.

Medical device 1 also includes a lumen 4 within housing 2 for receiving particles 101 from force applicator 11 and for receiving a pressurized fluid from a fluid source 7, via a channel 14, to propel particles 101 through lumen 4. Lumen 4 may be connected with or otherwise be in fluid communication with enclosure 5 storing agent 100, so that a distal portion of enclosure 5 transitions into lumen 4, as shown in FIG. 1A. Channel 14 includes a valve 17 along its length between source 7 and lumen 4, and is connected to a portion of lumen 4 that is distal to force applicator 11 to feed lumen 4 with pressurized fluid, thereby propelling particles 101 towards a distal end of lumen 4. Valve 14 is coupled to a trigger 15 located outside of a handle portion 3 of housing 2. Trigger 15 may be configured to at least open fluid valve 14, thereby providing a flow of pressurized fluid from fluid source 7 to lumen 4. Trigger 15 may be any suitable form, e.g., a button, a switch, and its form is not particularly limited. Fluid source 7 is within handle portion 3 of housing 2, but is not particularly limited to being within handle 3, and may even be outside housing 2. It is further noted that lumen 4 is not limited to being within housing 2, and in other embodiments, may be at least partially outside of housing 2. A catheter/sheath (not shown) may also be attached to (or otherwise extend from) the distal end of housing 2. Said catheter/sheath may be long, flexible to traverse tortuous patient anatomy, and any suitable size to insert into a working lumen of a scope (not shown) or another delivery device (not shown).

Medical device 1, shown in FIG. 1A, further includes a first gear 10 that is coupled to a surface of force applicator 11, and first gear 10 is configured to rotate simultaneously with force applicator 11, in the same direction. Medical device 1 also includes a lever 6 coupled to housing 2, and the coupled end of lever 6 includes a second gear 8. First gear 10 and second gear 8 are connected in series via a linking gear 9, positioned in between first gear 10 and second gear 8. Thus, lever 6 is pivotably coupled to linking gear 9, via second gear 8. As a result of such configuration, pulling lever 6 proximally rotates second gear 8 (clockwise as shown in FIG. 1A), which in turn rotates linking gear 9 (counter-clockwise), which rotates first gear 10 (clockwise) by a selected or desired degree. Pulling lever 6 proximally may entail translating one end of lever 6 (the end opposite of second gear 8) towards handle portion 3, as indicated by the directional arrow of FIG. 1A. This translation is a pivoted movement, as the other end of lever 6 (second gear 8) is pivotably connected to linking gear 9. The pulling of lever 6 may be by any suitable action, for example, by hand or by mechanical, electrical, or pneumatic action. The rotation of first gear 10 rotates force applicator 11 by a selected or desired degree, which proceeds to separate/crush a portion of agent 100, fed via drive wheels 13*a* and 13*b*, into particles 101. It is noted that the rotation of drive wheels 13*a* and 13*b* may be actuated via any suitable mechanism. Such mechanisms may include an automated mechanism that is triggered by the pulling of lever 6 or by the actuation of trigger 15 opening valve 17. Another mechanism may include an additional gear or a series of gears connecting first gear 10 to drive wheels 13*a* and 13*b*, and thus, also rotating said drive wheels by pulling lever 6.

Lever 6 further includes a contact 16, which may be a protrusion or a tab extending outward from the surface of lever 6 facing handle 3. Contact 16 may be configured to press or actuate trigger 15 on handle 3, as lever 6 is pulled proximally towards handle 3, thereby opening valve 17. Opening valve 17 permits pressurized fluid to flow into channel 14 past valve 17 and into lumen 4 to propel particles 101 distally. Referring to FIG. 1A, an example of how medical device 1 may be used is further discussed below. The distal portion of medical device 1 (e.g., a catheter or sheath having the distal portion of lumen 4) may be delivered into the body of a subject. Lumen 4 may be positioned so that a distal end of lumen 4 is adjacent to an intended target site for agent 100 administration. Such delivery and positioning may be accomplished via an endoscope having a working channel (not shown). Imaging associated with the endoscope may assist in positioning. A user may then load housing 2 of medical device 1 with agent 100, if not loaded already, so that wheels 13*a* and 13*b* of driving mechanism 13 may advance agent 100 towards force applicator 11. The manner in which housing 2 is loaded with agent 100 is not particularly limited. A user may then pull lever 6 proximally, by any suitable manner/mechanism, so that contact 16 presses against trigger 15, thereby opening valve 14 and providing a pressurized fluid to lumen 4, and also rotating force applicator 11 via the series of first gear 10, linking gear 9, and second gear 8. This results in force applicator 11 separating/crushing agent 100 into particles 101, via the force applied by teeth 12 to agent 100. Lumen 4 is fed with particles 101, which are propelled toward the distal end of lumen 4 via pressurized fluid and, thus, administered to the intended target site. Pulling lever 6 may also trigger a mechanism by which driving wheels 13*a* and 13*b* are rotated, such as via automated rotation or via a gear or a series of additional gears connecting first gear 10 to driving wheels 13*a* and 13*b*.

It is further noted that a throw of lever 6 rotates force applicator 11 by a certain degree, as discussed above, and supplies a continuous flow of pressurized fluid, as long as trigger 15 is pressed inward. Thus, a single throw of lever 6 may deliver a consistent, desired dose of agent 100, separated into particles 101, into lumen 4. For example, FIG. 1A shows that lever 6 may be rotated about 45 degrees clockwise, causing a set degree of rotation of gears 9, 10 and force applicator 11. This set amount of rotation corresponds to a set amount of agent 100 being separated into particles. For larger doses, a user may repeatedly actuate (push then pull) lever 6 so that force applicator 11 is intermittently rotated and pressurized fluid is supplied. Alternatively, for larger doses, the throw of lever 6 may be increased.

Medical device 1', as shown in FIG. 1B, is similar to device 1 in many respects. Like reference numeral refer to like parts. Differences between device 1 and 1' will be described. Device 1' includes an electric motor 20 coupled to force applicator 11, configured to rotate force applicator 11 electrically. In some other embodiments, medical device 1' may include a plurality of electric motors 20 and/or a plurality of force applicators 11. Medical device 1' further includes a battery 18 electrically connected to electric motor 20, via wires 19*a* and 19*b*, to power electric motor 20. Wire 19*a* connects the cathode of battery 18 to electric motor 20. Wire 19*b* includes two portions to connect the anode of battery 18 and motor 20 to trigger 15', which serves as both a valve switch and an electrical switch, along its path to electric motor 18. Therefore, the actuation of trigger 15' may open valve 17 and power electric motor 20 simultaneously in medical device 1'. The actuation of trigger 15' may be by any suitable action, for example, by hand or by mechanical, electrical, or pneumatic action.

Medical device 1' may be used in the same manner as medical device 1 except a user actuates trigger 15', as opposed to pulling a lever. The actuation of trigger 15' opens valve 14, thereby providing a pressurized fluid to lumen 4, and also powers the rotation of force applicator 11 via electric motor 20, which is electrically wired to battery 18. Additionally, the actuation of trigger 15' may also automate the rotation of driving wheels 13*a* and 13*b*, thereby feeding agent 100 to force applicator 11. Actuation of trigger 15' may operate the aforementioned functions in a continuous manner, until trigger 15' is released. Thus, a user may hold trigger 15' until a desired amount of agent 100, separated into particles 101, is delivered to a targeted site via lumen 4, and then release trigger 15' to cease the operation of device 1'.

FIG. 2 shows an example of another embodiment of drive mechanism 13'. Drive mechanism 13' includes a compressed spring 13*a'* coupled to a platform 13*b'* on one end, that is positioned adjacent to a proximal end of agent 100. Platform 13*b'* defines a surface which pushes against agent 100, as compressed spring 13*a'* decompresses, thereby pushing agent 100 towards a force applicator (not shown). The other end of spring 13*a'* is stationary against an inner surface of enclosure 5 in the housing. Agent 100 may be pre-loaded into enclosure 5, or enclosure 5 may include an opening/mechanism by which it may be loaded with agent 100. In this embodiment, a surface of one of the teeth, or any other force applying surface, of a force applicator (not shown)

may apply an opposite, greater force against spring 13a', so that spring 13a' remains compressed and agent 100 is not advanced. By such configuration, spring 13a' extends and agent 100 is advanced only when the force applicator is rotated or actuated.

Figure 3:
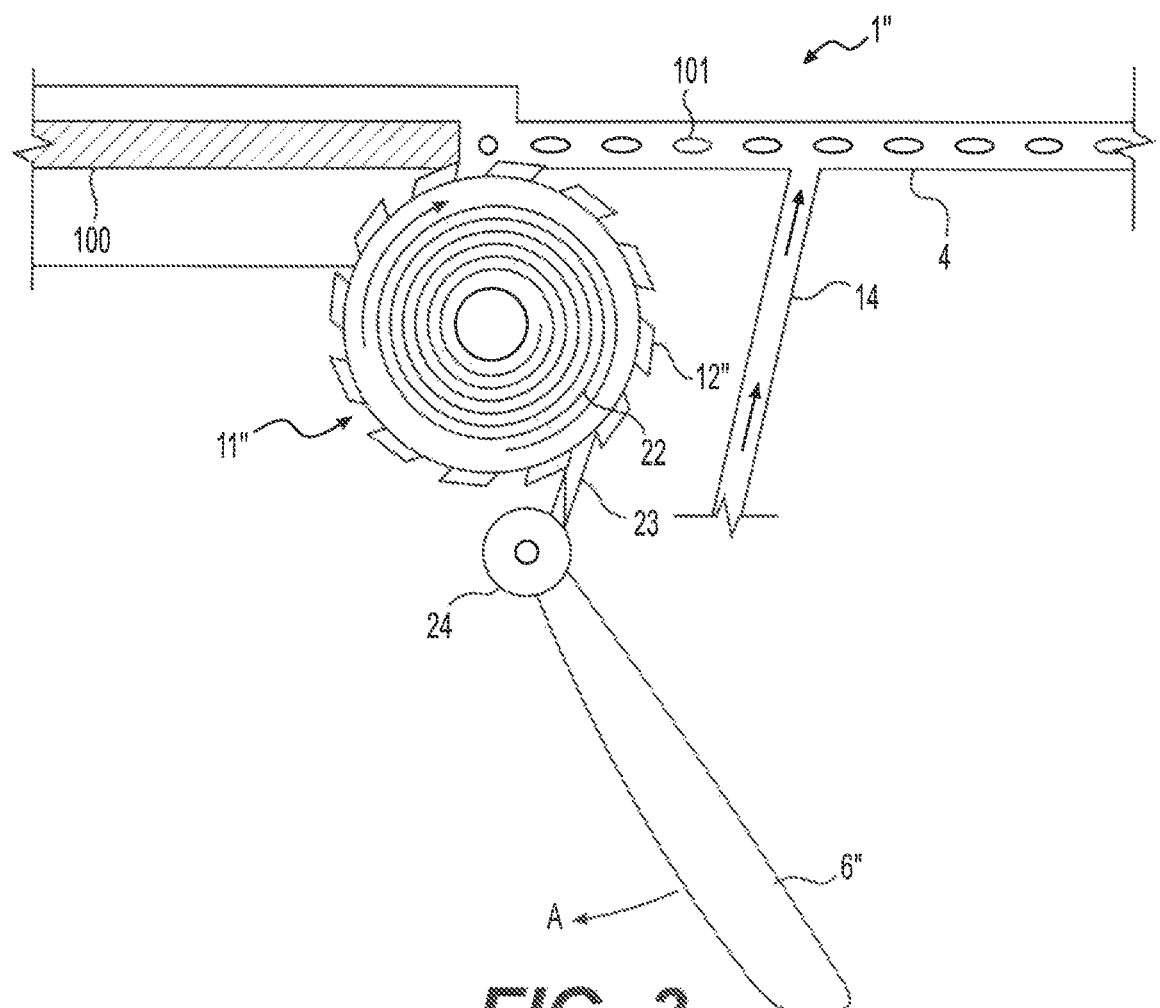
FIG. 3 is a cross-sectional view of a portion of a medical device, according to another embodiment.

FIG. 3 shows an example of another means by which force applicator 11 may be rotated in medical device 1" to apply a force separating/crushing agent 100 into particles 101. In medical device 1", a torsion spring 22 is coupled to force applicator 11 in a manner so that a torque or a rotary force actuates the rotation of force applicator 11". Medical device 1" further includes a lever 6" configured to pivot about a pivot point 24. Lever 6" includes a pawl 23 that may catch one of teeth 12" of force applicator 11", thereby inhibiting the rotation of force applicator 11". As lever 6" is pulled proximally (as shown by the arrow A), and pivots clockwise about pivot point 24, pawl 23 simultaneously rotates in a clockwise direction, and releases from one of teeth 12" of force applicator 11", thereby rotating force applicator 11" via the rotary force exerted by spring 22. As shown, the rotation of force applicator 11" applies a force to agent 100 via teeth 12", and separates/crushes agent 100 into particles 101, which are subsequently delivered to lumen 4. Thus, medical device 1" may be used in a similar manner as medical device 1. Medical device 1" may also be different in use than device 1. For example, lever 6" may be pulled (as shown by arrow A) and held in its pulled position to permit continuous rotation of force applicator 11', via the rotary force exerted by spring 22, and to have a constant supply of pressurized fluid. Thus, unlike device 1, multiple, sequential throws of lever 6" is not necessary to continually rotate force applicator 1" and supply pressurized fluid for a prolonged duration of time. Lever 6" may also be returned to its original position so that pawl 23 re-engages one of teeth 12" to inhibit further rotation of force applicator 11", and to also cease the supply of pressurized fluid to lumen 4. Lever 6" may be actuated by any suitable action, for example, by hand or by mechanical, electrical, or pneumatic action.

Figure 4A:
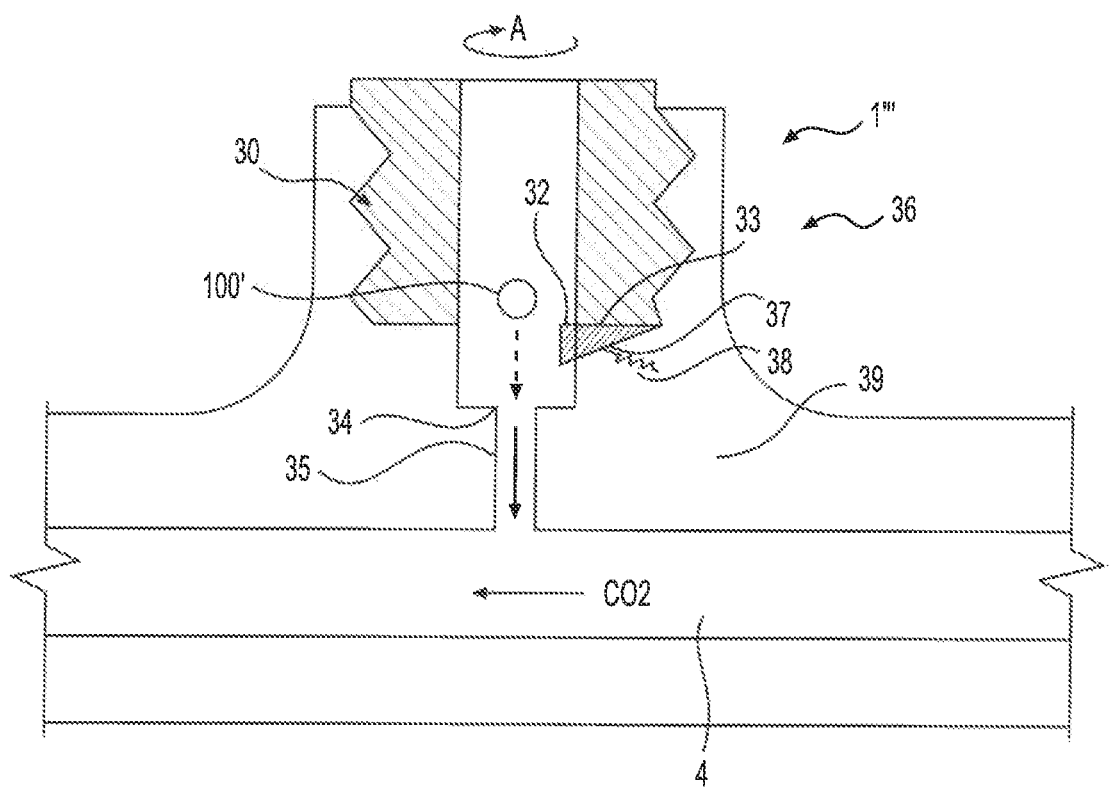
FIG. 4A is a cross-sectional view of a medical device, according to another embodiment.

Referring to FIGS. 4A-4D, another embodiment of medical device 1'" is described below. Medical device 1'" includes a housing 36 that includes a holster 30, which includes a plurality of cavities 31a-h for storing agent 100' in a first form, e.g., a pellet. Holster 30 sits within a enclosure of housing 36. FIG. 4A shows a cross-sectional view of holster 30 along line 4A-4A of FIG. 4B. Medical device 1'" also includes a lumen 4 receiving pressurized fluid, e.g., $CO_2$, from a fluid source (not shown) at its proximal end. Housing 36 includes a barrier region 39 positioned between holster 30 and lumen 4. As indicated by the directional arrow A in FIGS. 4A and 4B, holster 30 is rotatable relative to a remainder of housing 36 and lumen 4. Furthermore, housing 36 includes a force applicator in the form of a wedge 37, which defines a surface for applying a force to agent 100 to separate it into particles smaller than its first form. The form of a force applicator is not particularly limited to wedge 37, and may be any suitable form. Wedge 37 may be below holster 30, and may be spring-actuated, via spring 38. Any other form of biasing or pressing wedge 37 to the left in FIG. 1A may be used. In another embodiment, wedge 37 may be actuated via pneumatics. For example, an additional port or channel (not shown) may be branched from lumen 4 at a point that is proximal to a channel 35, so that said port may feed pressurized fluid directly into housing 36 or specifically towards wedge 37. The force of the fed pressurized fluid may engage wedge 37 to compress and crush agent 100'. In other embodiments, a combination of both a spring and pneumatics may be implemented to actuate wedge 37.

Figure 4B:
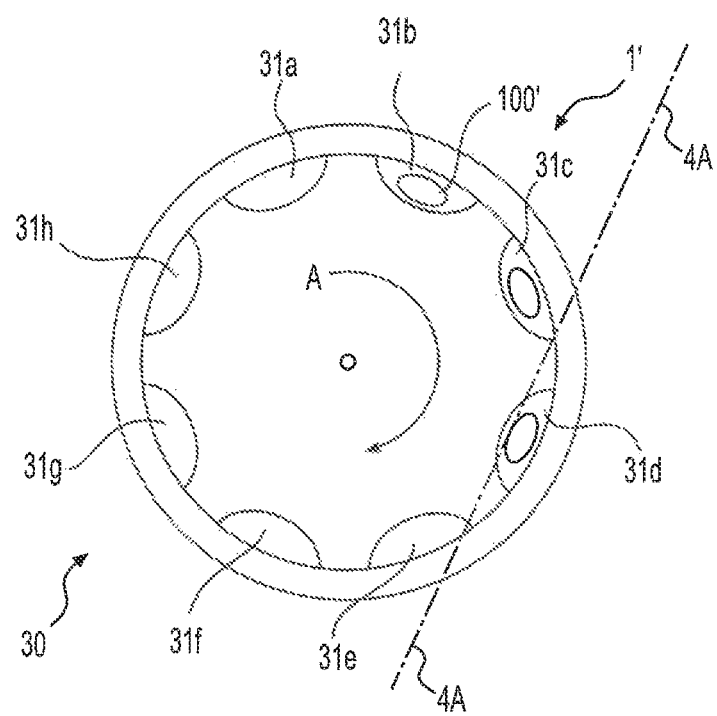
FIG. 4B is a top view of a holster of the medical device of FIG. 4A.
Figure 4C:
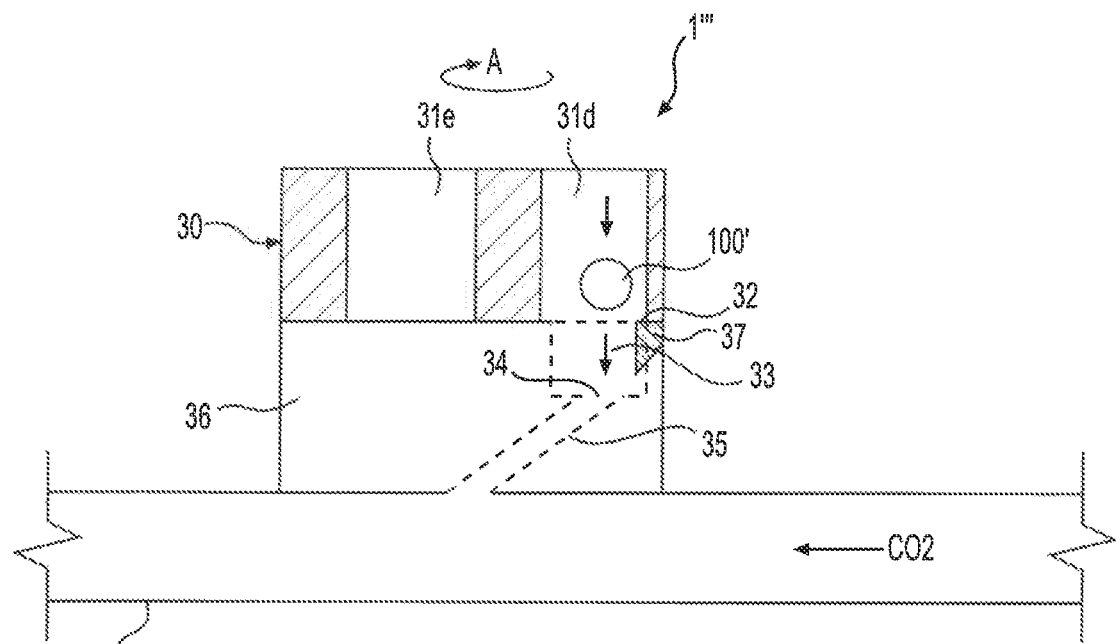
FIGS. 4C and 4D are cross-sectional views of a medical device, according to another embodiment.
Figure 4D:
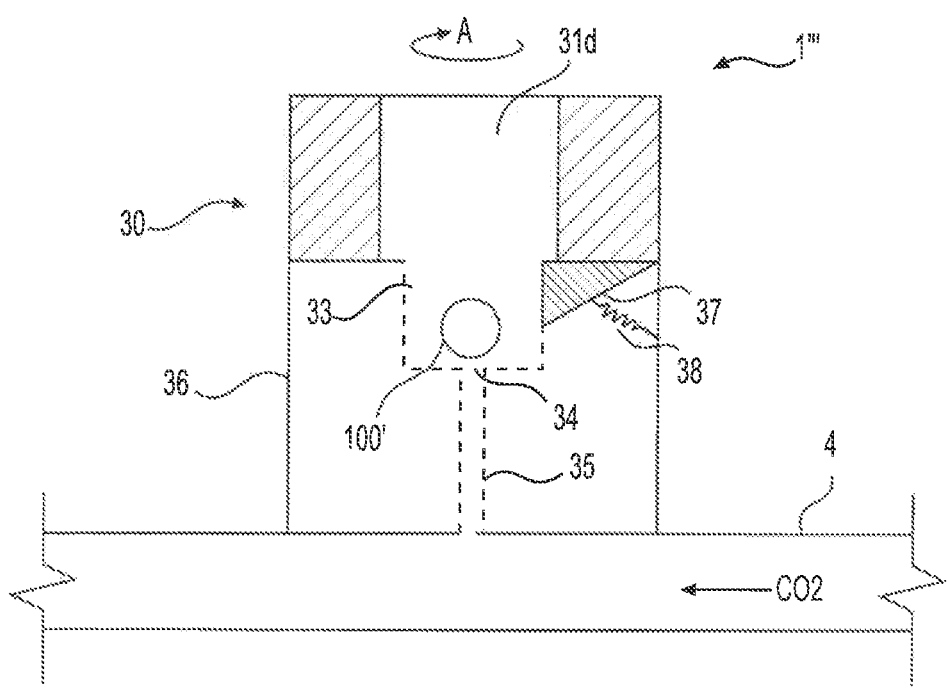

Housing 36 also includes a chamber 33 defined by a first opening 32 that is adjacent to holster 30, and a narrower, second opening 34 leading to a channel 35, which leads to lumen 4. First opening 32 may be aligned with any of the plurality of enclosures 31a-h of holster 30, depending on the rotational position of holster 30 relative to barrier 39. Thus, as holster 30 rotates, agent 100' may drop into chamber 33 from one of the plurality of enclosures 31a-h. The rotation of holster 30 may be by any suitable action, for example, by hand or by mechanical, electrical, or pneumatic action. For example, in some other embodiments, the rotation of holster 30 may be operated by a trigger that causes rotation or measured rotation of holster 30, e.g., rotation such that adjacent enclosures 31a-31h may be aligned with chamber 33 sequentially. In FIGS. 4A-4B, holster 30 includes eight enclosures 31a-h distributed evenly about the perimeter/circumference of holster 30. Actuation of a trigger may cause rotation of holster by 45 degrees to align a subsequent enclosure with opening 32. Although eight equally sized and spaced enclosures are shown, it is understood that there may be more or less number of enclosures, varied spacing, and varied size to accommodate different sizes/doses of agent 100'.

A portion of wedge 37, which may be spring-actuated via spring 38, obtrudes the enclosure defined by chamber 33, and after holster 30 releases agent 100' into chamber 33, wedge 37 separates/crushes agent 100' into particles (not shown). Because there is fluid communication between chamber 33 and lumen 4, via channel 35, the particles of agent 100' are delivered to lumen 4, and are propelled towards a distal end of lumen 4 via pressurized fluid. It is noted that agent 100', prior to being separated into particles, is inhibited from falling into channel 35 and being delivered to lumen 4 because second opening 34 and channel 35 are narrower than a width, or cross-sectional size, of agent 100', in whichever first form. A size of opening 34 and channel 35, and a force exerted by wedge 37, may control the size of particles delivered.

Referring to FIGS. 4A-4D, an example of how medical device 1'" may be used is further discussed below. Similar to the aforementioned exemplary medical devices, a distal portion of medical device 1'" (e.g., a catheter or sheath having the distal portion of lumen 4) may be delivered into the body of a subject. Lumen 4 may be positioned/directed so that a distal end of lumen 4 is adjacent an intended target site for agent 100 administration. As previously discussed, such delivery and positioning may be accomplished via an endoscope having a working channel (not shown). Imaging associated with the endoscope may assist in positioning. A user may then load one or more of the plurality of enclosures 31a-h of holster 30 with agent 100', if not loaded already. The user may then rotate holster 30 relative a remainder of housing 36 and lumen 4 so that one of enclosures 31a-31h aligns with first opening 32, thereby dropping agent 100' into chamber 33. Wedge 37 proceeds to apply a force onto agent 100', thereby separating/crushing agent 100' into particles (not shown). Rotation of holster 30 may be by any suitable manner or mechanism, e.g., by hand or by mechanical, electrical, or pneumatic action. Said rotation may also be a measured rotation or a continuous rotation via a mechanical or electrical means. Because there is fluid communication between chamber 33 and lumen 4, via channel 35, said particles are delivered to lumen 4, and are propelled towards a distal end of lumen 4 via pressurized fluid. It is noted that pressurized fluid may be supplied to lumen 4, by a fluid source, at any time prior to, during, and after the rotation of holster 30.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
   a housing that includes a holster defining a plurality of enclosures for storing agent in a first form;
   a force applicator within the housing and adjacent to at least one of the plurality of enclosures; and
   a drive mechanism for rotating the holster relative to the housing to align each of the plurality of enclosures with the force applicator, and moving the agent outwards from within each of the plurality of enclosures toward the force applicator, wherein the force applicator defines a surface for applying a force to the agent to separate the agent into particles smaller than a size of the first form;

wherein the device defines a lumen in fluid communication with the at least one of the plurality of enclosures for receiving the particles from the force applicator upon rotating the holster to align the at least one of the plurality of enclosures with the force applicator and the lumen, and the lumen is configured for receiving a pressurized fluid to propel the particles received from each of the plurality of enclosures through the lumen; and wherein each of the plurality of enclosures is configured to release the agent in the first form towards the force applicator via gravity upon alignment with the lumen.

2. The medical device of claim 1, wherein the force applicator includes a round gear including a plurality of teeth about a circumference of the round gear.

3. The medical device of claim 1, wherein the drive mechanism is connected to a trigger outside the housing, and actuation of the trigger causes rotation of the holster relative to the housing to align the plurality of enclosures with the force applicator.

4. The medical device of claim 1, further comprising a fluid source for providing the pressurized fluid, wherein the fluid source is connected to the lumen via a fluid channel, wherein the fluid channel is connected to a portion of the lumen distal to the force applicator; and wherein the force applicator is pneumatically actuated such that the pressurized fluid released by the fluid source is configured to move the force applicator relative to the at least one of the plurality of enclosures to separate the agent from the first form into the particles.

5. The medical device of claim 4, wherein the fluid channel includes a valve configured to open or close a flow of pressurized fluid from the fluid source to the lumen.

6. The medical device of claim 5, wherein the valve is coupled to a trigger, and the trigger is configured to at least open/close the valve.

7. The medical device of claim 1, further comprising:

an electric motor coupled to the force applicator, wherein the electric motor is configured to rotate the force applicator; and a battery electrically connected to the electric motor and a trigger, wherein the trigger is configured to act as an electrical switch that powers the electric motor via the battery.

8. The medical device of claim 7, wherein actuation of the trigger rotates the force applicator and continuously supplies pressurized fluid to the lumen from a fluid source, until the trigger is released.

9. The medical device of claim 1, wherein the housing further includes a chamber below the holster, and a channel between the chamber and the lumen so that there is fluid communication between the chamber and the lumen.

10. The medical device of claim 9, wherein the drive mechanism includes a rotation of the holster so that one of the plurality of enclosures aligns with the chamber, thereby delivering the agent from one of the enclosures to the chamber.

11. The medical device of claim 9, wherein the force applicator includes a wedge that obtrudes into the chamber, and the wedge is configured to separate the agent in the chamber into particles by cutting through the agent to reduce the size of the agent from the first form into the particles.

12. A medical device comprising:

a housing that includes a holster defining a plurality of enclosures for storing agent in a first form;

a force applicator within the housing and adjacent to at least one of the plurality of enclosures;

a drive mechanism for rotating the holster relative to the housing to align the at least one of the plurality of enclosures with the force applicator, and moving the agent stored therein toward the force applicator, wherein the force applicator is configured for applying a force to the agent to separate the agent into particles smaller than a size of the first form; and a lever coupled to the force applicator, wherein the lever is configured for moving the force applicator to apply the force to the agent, thereby separating the agent into the particles;

wherein the device defines a lumen for receiving the particles from the at least one of the plurality of enclosures upon the holster rotating the housing to align the force applicator with the at least one of the plurality of enclosures, wherein each of the plurality of enclosures is configured to release the agent in the first form towards the force applicator via gravity upon alignment with the lumen and the lumen is configured for receiving a pressurized fluid to propel the particles through the lumen.

13. The medical device of claim 12, wherein the drive mechanism is connected to a trigger outside the housing, and actuation of the trigger operates the drive mechanism.

14. The medical device of claim 12, further comprising a fluid source for providing the pressurized fluid, wherein the fluid source is connected to the lumen via a fluid channel, and wherein the fluid channel includes a valve configured to open or close a flow of pressurized fluid from the fluid source to the lumen; and wherein the flow of pressurized fluid released from the fluid source is configured to move the force applicator relative to the at least one of the plurality of enclosures to cut the agent from the first form into the particles.

15. The medical device of claim 14, wherein actuation of the lever actuates a trigger to supply the pressurized fluid to the lumen.

16. A medical device comprising:

a housing including a plurality of enclosures and an opening, each of the plurality of enclosures is configured to store an agent in a first form, wherein the plurality of enclosures is configured to rotate relative to the opening to align at least one of the plurality of enclosures with the opening;

a force applicator positioned adjacent to the opening;

a drive mechanism configured to rotate the plurality of enclosures relative to the opening, and release the agent stored in the at least one of the plurality of enclosures towards the opening upon alignment with the opening, wherein the force applicator is configured to separate the agent stored in the at least one of the plurality of enclosures into particles that are smaller than a size of the first form upon the at least one of the plurality of enclosures releasing the agent towards the opening, wherein each of the plurality of enclosures is configured to release the agent in the first form towards the force applicator via gravity upon alignment with the opening; and a lumen in fluid communication with the at least one of the plurality of enclosures and a pressurized fluid from a fluid source, the lumen is configured to:

receive the particles from the at least one of the plurality of enclosures upon rotating the plurality of enclosures and aligning the at least one of the plurality of enclosures with the opening; and propel the particles received from the at least one of the plurality of enclosures through the lumen with the pressurized fluid.

17. The medical device of claim 16, wherein the lumen includes a first cross-sectional dimension that is smaller than a second cross-sectional dimension of the agent in the first form, such that the lumen is configured to inhibit receipt of the agent in the first form prior to the force applicator separating the agent into the particles.

18. The medical device of claim 16, further comprising a fluid source configured to supply the pressurized fluid to the lumen; and wherein the force applicator is pneumatically actuated such that the pressurized fluid released by the fluid source is configured to move the force applicator relative to the at least one of the plurality of enclosures to seperate the agent from the first form into the particles.

19. The medical device of claim 16, further comprising a biasing mechanism coupled to the force applicator, wherein the biasing mechanism is configured to push the force applicator towards the agent stored in the at least one of the plurality of enclosure upon aligning the at least one of the plurality of enclosure with the force applicator.

* * * * *